United States Patent
Goto et al.

(10) Patent No.: US 9,234,260 B2
(45) Date of Patent: Jan. 12, 2016

(54) METHOD FOR ISOLATING VALUABLE METAL

(71) Applicants: Kyushu University, National University Corporation, Fukuoka-shi, Fukuoka (JP); SUMITOMO METAL MINING CO., LTD., Tokyo (JP)

(72) Inventors: Masahiro Goto, Fukuoka (JP); Fukiko Kubota, Fukuoka (JP); Yuzo Baba, Fukuoka (JP)

(73) Assignees: KYUSHU UNIVERSITY, NATIONAL UNIVERSITY CORPORATION, Fukuoka-shi (JP); SUMITOMO METAL MINING CO., LTD., Tokyo (JP)

( * ) Notice: Subject to any disclaimer, the term of this patent is extended or adjusted under 35 U.S.C. 154(b) by 0 days.

(21) Appl. No.: 14/423,079

(22) PCT Filed: Apr. 26, 2013

(86) PCT No.: PCT/JP2013/062482
§ 371 (c)(1),
(2) Date: Feb. 20, 2015

(87) PCT Pub. No.: WO2014/030396
PCT Pub. Date: Feb. 27, 2014

(65) Prior Publication Data
US 2015/0240329 A1 Aug. 27, 2015

(30) Foreign Application Priority Data
Aug. 20, 2012 (JP) .................. 2012-181886

(51) Int. Cl.
*C22B 58/00* (2006.01)
*C22B 3/44* (2006.01)
(Continued)

(52) U.S. Cl.
CPC ............ *C22B 58/00* (2013.01); *B01D 11/0492* (2013.01); *C07D 233/64* (2013.01);
(Continued)

(58) Field of Classification Search
CPC ........ C22B 58/00; C22B 3/0032; C22B 3/44; B01D 11/0492
See application file for complete search history.

(56) References Cited

U.S. PATENT DOCUMENTS

| | | | | |
|---|---|---|---|---|
| 5,204,074 | A * | 4/1993 | Pescher et al. | 423/112 |
| 5,344,567 | A * | 9/1994 | Rickelton | 210/638 |
| 2011/0005354 | A1* | 1/2011 | Bednarski et al. | 75/721 |

FOREIGN PATENT DOCUMENTS

| | | |
|---|---|---|
| JP | H04-048038 | 2/1992 |
| JP | 2000-212658 A | 8/2000 |
| JP | 2012-102062 A | 5/2012 |

OTHER PUBLICATIONS

Morizono Hirofumi et al., "Liquid-liquid extraction of transition metal ions with an alkylhistidine extractant", Separation and Purification Technology, vol. 80 No. 2, Jul. 29, 2011, p. 390-395.

(Continued)

*Primary Examiner* — George Wyszomierski
*Assistant Examiner* — Tima M McGuthry Banks
(74) *Attorney, Agent, or Firm* — Locke Lord LLP

(57) ABSTRACT

Provided is a method that selectively extracts and, at a low cost, recovers indium from an acidic solution containing indium and gallium. The present invention is a method that is for isolating a valuable metal and that, by means of subjecting an acidic solution containing indium and gallium to a solvent extraction that is by means of an extraction agent comprising an amide derivative represented by a general formula, extracts indium from the acidic solution. In the formula, $R^1$ and $R^2$ each indicate the same or a different alkyl group, $R^3$ indicates a hydrogen atom or an alkyl group, and $R^4$ indicates a hydrogen atom or any given group, other than an amino group, bonded to the α-carbon as an amino acid. The general formula preferably has a glycine unit, a histidine unit, a lysine unit, an aspartic acid unit, or an N-methylglycine unit.

20 Claims, 7 Drawing Sheets

(51) Int. Cl.
    *B01D 11/04* (2006.01)
    *C07D 233/64* (2006.01)
    *C22B 3/26* (2006.01)
    *C22B 3/06* (2006.01)
    *C22B 19/00* (2006.01)

(52) U.S. Cl.
    CPC ............... *C22B3/0032* (2013.01); *C22B 3/06* (2013.01); *C22B 3/44* (2013.01); *C22B 19/00* (2013.01); *C08J 2205/10* (2013.01); *Y02P 10/234* (2015.11)

(56) References Cited

OTHER PUBLICATIONS

International Search Report of PCT/JP2013/062482 dated Jul. 29, 2013.

\* cited by examiner

METHOD FOR ISOLATING VALUABLE METAL

CROSS-REFERENCE TO RELATED APPLICATIONS

This application is the national phase under 35 U.S.C. §371 of PCT International Application No. PCT/JP2013/062482, filed Apr. 26, 2013, which claims the benefit of Japanese Application No. 2012-181886, filed Aug. 20, 2012, the entire contents of the aforementioned applications are hereby incorporated herein by reference.

TECHNICAL FIELD

The present invention relates to a method for isolating a valuable metal, more particularly, a method for efficiently extracting indium from an acidic solution containing indium and gallium and isolating indium and gallium.

BACKGROUND ART

Indium is supplied in the form of alloy targets with zinc and tin and paste as a material for transparent conductive films such as a semiconductor device and a touch panel and is widely used.

Ores incidentally contain indium in a very slight amount and also indium is unevenly distributed. So it is not easy to ensure a stable supply of indium. In addition, ores containing indium contain lead and zinc in a grossly excessive amount as compared to the amount of indium in many cases. Thus, when recovering indium there is a great problem with efficiently separating indium from lead and zinc.

Therefore, indium is obtained from ores, and furthermore indium is also obtained by recovering electronic circuit boards discarded in the city, defective items produced in production processes and, further, target materials which have been effectively finished and the like and recycling these. When the discarded electronic circuit boards and the like are recycled to obtain indium, however, there is still a problem with efficiently separating indium from gallium because indium and many types of valuable metal including gallium coexist in the discarded electronic circuit boards and the like.

As a method for extracting indium, a solution obtained by a two-stage neutralization treatment during the zinc leaching residue treatment step of zinc smelting is used as a solution to be extracted containing indium and gallium, and this solution to be extracted is adjusted to pH 2.4 to 3.6. Separately, a chelating agent is added to an organic solvent, and an extraction organic solvent having an organic phase in which a part of the protons in this chelating agent is substituted by an alkaline earth metal is also prepared. It is proposed that both these solutions be mixed to extract and isolate indium and gallium in the above solution to be extracted (see Patent Document 1). The method described in Patent Document 1, however, cannot be directly applied to a solution leached using an acid, for example, a low pH solution with a pH less than 2, and costs for a neutralizer to adjust pH, neutralization equipment, and much time for treatment are required.

Patent Document 1: Japanese Unexamined Patent Application, Publication No. 2000-212658

DISCLOSURE OF THE INVENTION

Problems to be Solved by the Invention

An object of the present invention is to provide a method which selectively extract and, at a low cost, recover indium from an acidic solution containing indium and gallium.

As a result of repeated intensive research to solve the above problems, the present inventors found that the above object could be achieved by providing a valuable metal extraction agent comprising an amide derivative represented by the following general formula (I), thereby completing the present invention.

Means for Solving the Problems

Specifically, the following are provided in the present invention.

(1) The present invention is a method for isolating a valuable metal, wherein an acidic solution containing indium and gallium is subjected to solvent extraction by an extraction agent comprising an amide derivative represented by the following general formula (1) to isolate indium and gallium from the acidic solution:

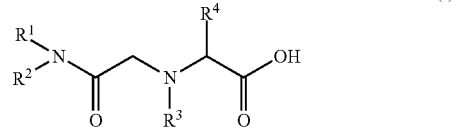

(wherein $R^1$ and $R^2$ each represents the same or different alkyl group, the alkyl group may be a straight chain or a branched chain, $R^3$ represents a hydrogen atom or an alkyl group, and $R^4$ represents a hydrogen atom or any group other than an amino group which is bound to the α carbon as an amino acid).

(2) in addition, the present invention is the method for isolating a valuable metal according to (1), wherein the amide derivative is any one or more of a glycine amide derivative, a histidine amide derivative, a lysine amide derivative, an aspartic acid amide derivative and a normal-methylglycine derivative.

(3) In addition, the present invention is the method for isolating a valuable metal according to (2), wherein the amide derivative is the glycine amide derivative and the acidic solution is subjected to the solvent extraction with the pH of the acidic solution adjusted to a range of between 0.7 or more to 1.9 or less.

(4) In addition, the present invention is the method for isolating a valuable metal according to (2), wherein the amide derivative is the histidine amide derivative and the acidic solution is subjected to the solvent extraction with the pH of the acidic solution adjusted to a range of between 0.7 or more to 3.0 or less.

(5) In addition, the present invention is the method for isolating a valuable metal according to (2), wherein the amide derivative is the normal-methylglycine derivative and the acidic solution is subjected to the solvent extraction with the pH of the acidic solution adjusted to a range of between 0.7 or more to 2.3 or less.

(6) In addition, the present invention is a method for isolating a valuable metal according to any of (1) to (5), wherein, an acidic solution with a pH of 0.6 or less is mixed with the extraction agent which has extracted the indium from the acidic solution to carry out back extraction, and, thereafter, the extraction agent and the acidic solution are separated to obtain the acidic solution containing the indium.

(7) In addition, the present invention is the method for isolating a valuable metal according to (6), wherein, an acidic solution is mixed with the extraction agent which has extracted the indium from the acidic solution, and the extraction agent and the acidic solution are then separated to remove gallium from the extraction agent and the back extraction is then carried out.

(8) In addition, the present invention is the method for isolating a valuable metal according to (7), wherein the amide derivative is the glycine amide derivative, and, an acidic solution with a pH of 1.1 or more and 1.4 or less is mixed with the extraction agent which has extracted the indium from the acidic solution, and the extraction agent and the acidic solution are then separated to remove gallium from the extraction agent and the back extraction is then carried out.

(9) In addition, the present invention is the method for isolating a valuable metal according to (7), wherein the amide derivative is the histidine amide derivative, and, an acidic solution with a pH of 1.5 or more and 1.8 or less is mixed with the extraction agent which has extracted the indium from the acidic solution, and the extraction agent and the acidic solution are then separated to remove gallium from the extraction agent and the back extraction is then carried out.

(10) In addition, the present invention is the method for isolating a valuable metal according to (7), wherein the amide derivative is the normal-methylglycine derivative, and an acidic solution with a pH of between 1.4 or more and 1.8 or less is mixed with the extraction agent which has extracted the indium from the acidic solution, and the extraction agent and the acidic solution are then separated to remove gallium from the extraction agent and the back extraction is then carried out.

(11) In addition, the present invention is a method for isolating a valuable metal according to any of (1) to (10), wherein the acidic solution containing indium and gallium is a solution obtained by mixing sulfuric acid with a member containing indium and gallium and not containing cadmium and leaching indium and gallium from the member.

Effects of the Invention

According to the present invention, indium can be efficiently extracted from an acidic solution containing both indium and gallium. In addition, the number of extraction steps can be decreased in actual operation and the equipment size can be compressed, and thus indium and gallium can be isolated and recovered at a low cost.

PREFERRED MODE FOR CARRYING OUT THE INVENTION

Figure 1:
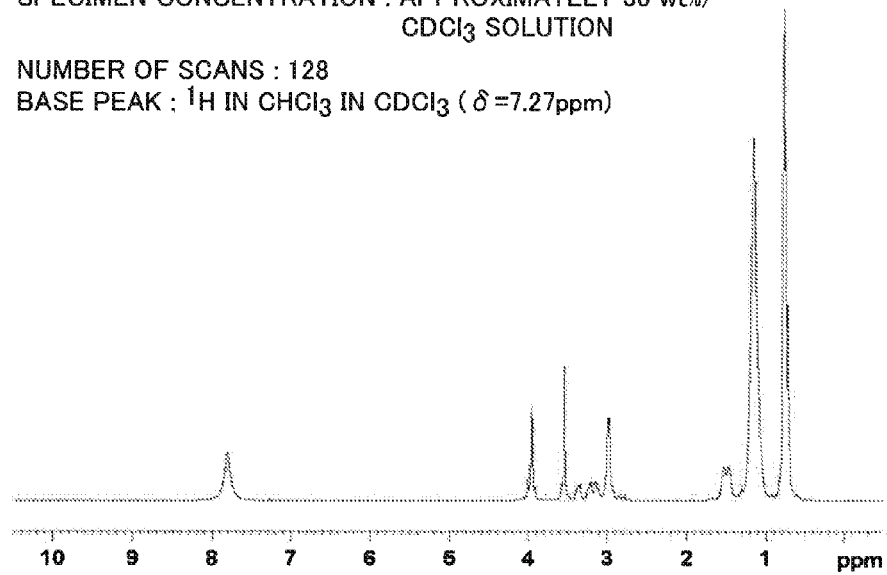
FIG. 1 is a diagram showing the $^1$H-NMR spectrum of a glycine amide derivative involved in Synthetic Example 1.

Specific embodiments of the present invention will be now described in detail. It is noted, however, that the present invention is not limited to the following embodiments, and can be properly changed within the scope of the object of the present invention and carried out.

Extraction Agent

The extraction agent used for indium extraction comprises an amide derivative represented by the following general formula (I).

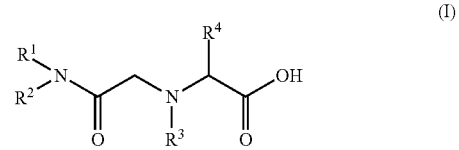

In the formula, the substituents $R^1$ and $R^2$ each represent the same or different alkyl group. The alkyl group may be a straight chain or a branched chain. $R^3$ represents a hydrogen atom or an alkyl group. $R^4$ represents a hydrogen atom or any group other than an amino group which is bound to the α carbon as an amino acid. In the present invention, lipophilicity is enhanced by introducing an alkyl group into the amide skeleton and the present invention can be used as an extraction agent.

The above amide derivative is any one or more of a glycine amide derivative, a histidine amide derivative, a lysine amide derivative, an aspartic acid amide derivative and a normal-methylglycine derivative (also referred to as a sarcosine amide derivative).

When the amide derivative is a glycine amide derivative, the above glycine amide derivative can be synthesized by the following method. First, a 2-halogenated acetyl halide is added to an alkyl amine having a structure represented by $NHR^1R^2$ ($R^1$ and $R^2$ are the same as the above substituents $R^1$ and $R^2$) and the hydrogen atom of the amine is substituted with a 2-halogenated acetyl by a nucleophilic substitution reaction to obtain a 2-halogenated (N,N-di)alkylacetamide.

Next, the above 2-halogenated (N,N-di)alkylacetamide is added to a glycine or N-alkyl glycine derivative, and one hydrogen atom of the glycine or N-alkyl glycine derivative is substituted with a (N,N-di)alkylacetamide group by a nucleophilic substitution reaction. With the two-step reaction, a glycine alkyl amide derivative can be synthesized.

It is noted that by replacing glycine with histidine lysine, aspartic acid or normal-methylglycine, a histidine amide derivative, a lysine amide derivative, an aspartic acid amide derivative or a normal-methylglycine derivative can be synthesized.

Extraction of Indium

To extract indium ions using an extraction agent synthesized by the above method, the pH of an acidic aqueous solution containing indium ions is adjusted and then the acidic solution is added to an organic solution having the above extraction agent as a component, and mixed. Therefore, an objective valuable metal ion can be selectively extracted in the organic phase. It is noted that by adjusting the above extraction agent to an appropriate concentration using a known diluent and the like as required, isolation ability can be improved and operation can be stabilized.

After the extraction of indium ions, an acidic solution adjusted to a lower pH than that of the above acidic aqueous solution is added to the organic solvent as a back extraction starting solution and stirred to isolate an objective indium ion by extraction to the organic solvent. Furthermore, by the back extraction of the objective indium ion from the organic solvent, the objective indium ion can be recovered in the aqueous solution. For example, an aqueous solution in which nitric acid, hydrochloric acid or sulfuric acid is diluted is suitably used as the back extraction solution. In addition, indium ions can be also concentrated by properly changing the ratio of organic phase and aqueous phase.

The organic solvent can be any solvent in which an extraction agent and metal extraction species are dissolved, and examples thereof include chlorine solvents such as chloroform and dichloromethane, aromatic hydrocarbons such as benzene, toluene and xylene, aliphatic hydrocarbons such as hexane, and the like. These organic solvents may be used alone or two or more solvents may be used in combination. Alcohols such as 1-octanol may be mixed.

The concentration of the extraction agent can be properly set depending on the concentration of indium and gallium. In addition, the stirring time and extraction temperature may be properly set depending on the conditions of the acidic aqueous solution of indium ions and the organic solution of the extraction agent.

To efficiently recover indium from an acidic aqueous solution containing indium and gallium, by adding an alkali, an acid or the like to the acidic aqueous solution containing indium and gallium, the acidic aqueous solution may be adjusted within the pH range in which indium is extracted and the extraction of gallium is inhibited.

When extraction is carried out in the pH region in which the extraction rate of indium is low, the amount of indium extracted, i.e., the recovery rate declines. Contrarily, when extraction is carried out in the pH region in which the extraction rate is excessively high, gallium is also extracted and thus isolation of indium and gallium is insufficient.

Multistep extraction is therefore industrially carried out in many cases. Indiscriminately increasing the number of extraction steps, however, is not preferred in terms of equipment investment and costs. Like the present invention, in particular, in the field which tries to isolate indium from scrap and ores and the like, it is thought that extraction with 3 or 4 or less steps at the most is practical in terms of the liquid volume to be treated and the like. Because of this the extraction rate of indium in one step extraction is preferably 50% or more, more preferably 80% or more and even more preferably 95% or more. Contrarily, the extraction rate of gallium, which is an impurity, is preferably 20% or less and more preferably 10% or less.

The basic structure of the extraction aeents used in the present invention is the same, but the small difference in optimum pH region is caused by a small difference in structure, and the agents can be properly used depending on the target liquids and conditions.

When the extraction agent is a glycine amide derivative, for example, the pH is preferably adjusted to between 0.7 or more and 1.9 or less and more preferably adjusted to between 1.0 or more and 1.2 or less.

In addition, when the extraction agent is a histidine amide derivative, the pH is preferably adjusted to between 0.7 or more and 3.0 or less and more preferably adjusted to between 1.1 or more and 1.8 or less.

In addition, when the extraction agent is a normal-methylglycine derivative, the pH is preferably adjusted to between 0.7 or more and 2.3 or less and more preferably adjusted to between 1.2 or more and 1.5 or less.

By bringing an organic solution after extraction, with which indium has been extracted, into contact with an acidic solution having a lower pH than that of the original acidic solution as a back extraction starting solution, incidentally, indium in an extraction agent is distributed into the back extraction starting solution to recover indium, and simultaneously the extraction agent can be regenerated. The pH of the back extraction starting solution is preferably low in the respect in which indium can be recovered with high efficiency, but when the pH is too low, the recovery rate is not improved to more than a certain level and costs also increase. Further, when the pH is too low, there are problems in that, for example, the decomposition of an extraction agent is promoted. Therefore, the pH is preferably in the range of between 0.4 or more to 0.8 or less.

In addition, before the above back extraction of an extraction agent which has extracted indium, the extraction agent is brought into contact with an acidic solution for washing (also referred to as scrubbing), thereby being able to isolate a part of the extracted gallium from the extraction agent. Consequently, the purity of the indium obtained by back extraction can be improved. When the range in which the extraction rate of indium is 90 to 95% or more and the extraction rate of gallium is almost 0% is used as a standard, it is preferred that the acidic solution added in the washing step be pH 1.1 or more and 1.4 or less in an extraction agent comprising a glycine amide derivative, pH 1.5 or more and 1.8 or less in an extraction agent comprising a histidine amide derivative, and pH 1.4 or more and 1.8 or less in an extraction agent comprising a sarcosine amide derivative.

EXAMPLES

The present invention will be now described in more detail by way of examples thereof. It is noted, however, that the present invention is not limited to these descriptions.

Synthetic Example 1

Synthesis of Extraction Agent Comprising Glycine Amide Derivative

As an example of amide derivatives forming an extraction agent, a glycine amide derivative represented by the following general formula (III) was synthesized, that is, N-[N,N-bis(2-ethylhexyl)aminocarbonylmethyl]glycine (or also referred to as N,N-di(2-ethylhexyl)acetamide-2-glycine, hereinafter referred to as "D2EHAG") into which two 2-ethylhexyl groups were introduced.

D2EHAG was synthesized as follows. First, as shown in the following reaction formula (II), 23.1 g (0.1 mol) of commercially available di(2-ethylhexyl)amine and 10.1 g (0.1 mol) of triethylamine were taken and chloroform was added thereto and dissolved. Next, 13.5 g (0.12 mol) of 2-chloroacetyl chloride was added dropwise thereto and the obtained mixture was washed once with 1 mol/l hydrochloric acid and then washed with ion exchanged water, and the chloroform phase was separated.

Next, anhydrous sodium sulfate was added thereto in an appropriate amount (approximately 10 to 20 g) for dehydration, followed by filtration to obtain 29.1 g of yellow liquid. The structure of this yellow liquid (reaction product) was identified using a nuclear magnetic resonance analyzer (NMR) and the above yellow liquid was confirmed to have the structure of 2-chloro-N,N-di(2-ethylhexyl)acetamide (hereinafter, referred to as "CDEHAA"). It is noted that the field of CDEHAA was 90% with respect to di(2-ethylhexyl)amine, which is a raw material.

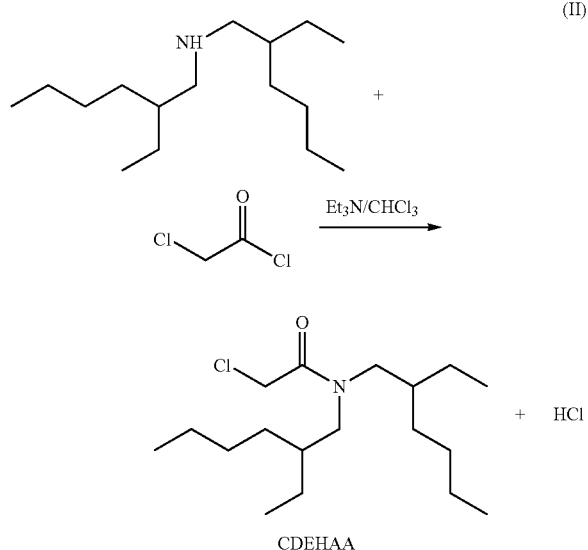

CDEHAA

Next, as shown in the following reaction formula (III), 8.0 g (0.2 mol) of sodium hydroxide was dissolved by adding methanol, and 15.01 g (0.2 ml) of glycine were also added thereto. While stirring the obtained solution, 12.72 g (0.04 mol) of the above CDEHAA were slowly added dropwise thereto and stirred. After completion of stirring, the solvent in the reaction liquid was distilled off and the residue was dissolved by adding chloroform. This solution was acidified by adding 1 mol/l sulfuric acid and then washed with ion exchanged water, and the chloroform phase was separated.

Figure 2:
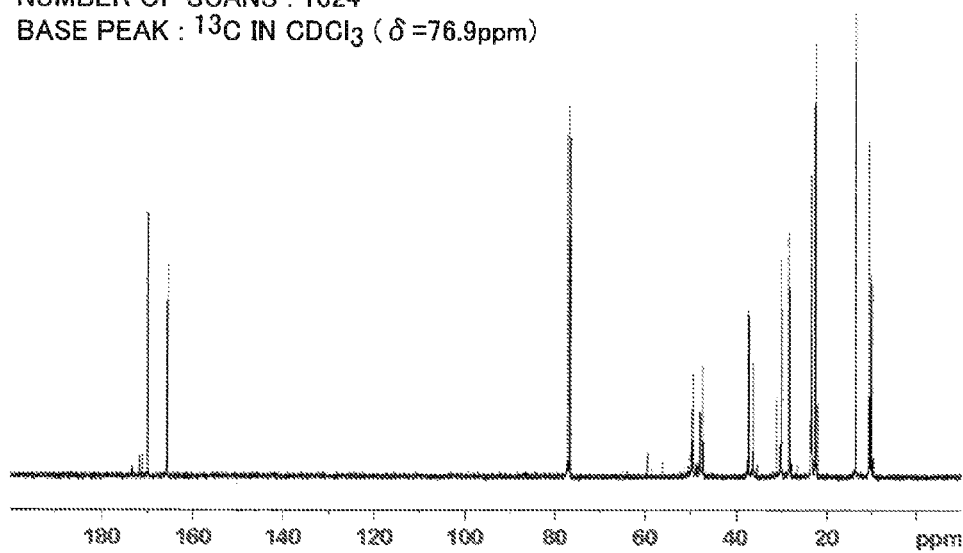
FIG. 2 is a diagram showing the $^{13}$C-NMR spectrum of a glycine amide derivative involved in Synthetic Example 1.

Anhydrous magnesium sulfate was added to this chloroform phase in an appropriate amount for dehydration, followed by filtration. The solvent was removed under reduced pressure again to obtain 12.5 g of yellow paste. The yield was 87% based on the amount of the above CDEHAA. The structure of the yellow paste was identified by NMR and elemental analysis and the yellow paste was confirmed to have the structure of D2EHAG as shown in FIG. 1 and FIG. 2. The extraction agent in Synthetic Example 1 was obtained by undergoing the above steps.

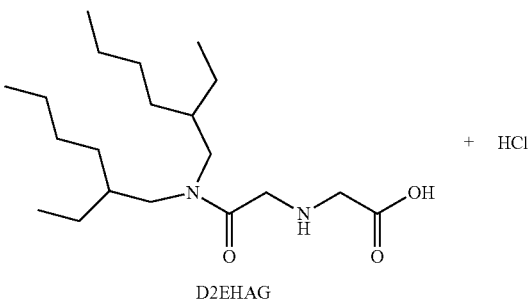

D2EHAG

Synthetic Example 2

Synthesis of Extraction Agent Comprising Histidine Amide Derivative

As another example of amide derivatives forming an extraction agent, a histidine amide derivative represented by the following general formula (IV) was synthesized, that is, N-[N,N-bis(2-ethylhexyl)aminocarbonylmethyl]histidine (or also referred to as N,N-di(2-ethylhexyl)acetamide-2-histidine, hereinafter referred to as "D2EHAH") into which two 2-ethylhexyl groups were introduced.

D2EHAS was synthesized as follows. As shown in the following reaction formula (IV), 5.3 g (0.132 mol) of sodium hydroxide were dissolved by adding methanol, and 11.8 g (0.132 mol) of sarcosine (N-methylglycine) were also added thereto. While stirring the obtained solution, 36.3 g (0.12 mol) of the above CDEHAA were slowly added dropwise thereto and stirred. After completion of stirring, the solvent in the reaction liquid was distilled off and the residue was dissolved by adding chloroform. This solution was acidified by adding 1 mol/l sulfuric acid and then washed with ion exchanged water, and the chloroform phase was separated.

Anhydrous magnesium sulfate was added to this chloroform phase in an appropriate amount for dehydration, followed by filtration. The solvent was removed under reduced pressure again to obtain 26.8 g of yellowish brown paste. The yield was 60% based on the amount of the above CDEHAA. The structure of the yellow paste was identified by NMR and elemental analysis and the yellow paste was confirmed to have the structure of D2EHAS. The extraction agent in Synthetic Example 2 was obtained by undergoing the above steps.

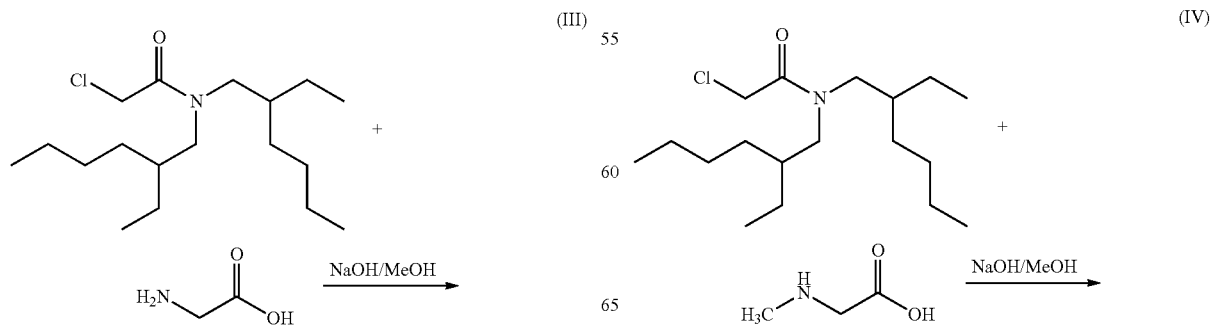

-continued

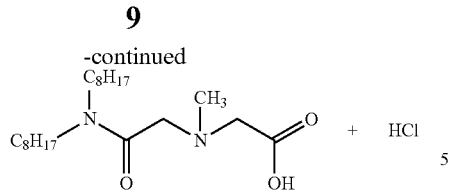

Synthetic Example 3

Synthesis of Extraction Agent Comprising Normal-Methylglycine Derivative

As another example of amide derivatives forming an extraction agent, a normal-methylglycine derivative represented by the following general formula (I) was synthesized, that is, N-[N,N-bis(2-ethylhexyl)aminocarbonylmethyl]sarcocine (or also referred to as N,N-di(2-ethylhexyl)acetamide-2-sarcocine, hereinafter referred to as "D2EHAS") into which two 2-ethylhexyl groups were introduced.

D2EHAH was synthesized as follows. As shown in the following reaction formula (V), 16 g (0.04 mol) of sodium hydroxide were dissolved by adding methanol, and 31.0 g (0.2 mol) of histidine were also added thereto. While stirring the obtained solution, 13.2 g (0.04 mol) of the above CDEHAA were slowly added dropwise thereto. After completion of dropwise addition, the solution was stirred with alkaline conditions maintained. After completion of stirring, the solvent in the reaction liquid was distilled off and the residue was dissolved by adding ethyl acetate. This solution was washed and the ethyl acetate phase was separated.

Anhydrous magnesium sulfate was added to this ethyl acetate phase in an appropriate amount for dehydration, followed by filtration. The solvent was removed under reduced pressure again to obtain 9.9 g of yellowish brown paste. The yield was 57% based on the amount of the above CDEHAA. The structure of the yellowish brown paste was identified by NMR and elemental analysis and the yellowish brown paste was confirmed to have the structure of D2EHAH. The extraction agent in Synthetic Example 3 was obtained by undergoing the above steps.

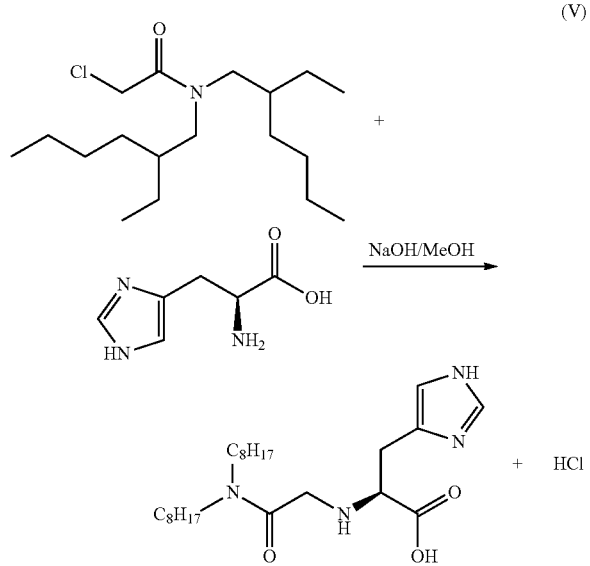

(V)

Extraction of Indium

Using the extraction agents in Synthetic Examples 1 to 3, indium was extracted and isolated.

Example 1

An original liquid containing 8 mg/l indium and 5 mg/l gallium was divided into 3 ml portions, and sulfuric acid was added to these to adjust the pH to from 0.8 to 3.7. The several types of sulfuric acidic solution and an n-dodecane solution with the same volume as above (3 ml) having the extraction agent involved in Synthetic Example 1 at a concentration of 0.01 mol/l were added to test tubes. The test tubes were put into a thermostatic chamber at 25° C. and shaken. At this time, the pH of the sulfuric acid solutions was adjusted using 0.1 mol/l nitric acid, ammonium nitrate and ammonia.

Figure 3:
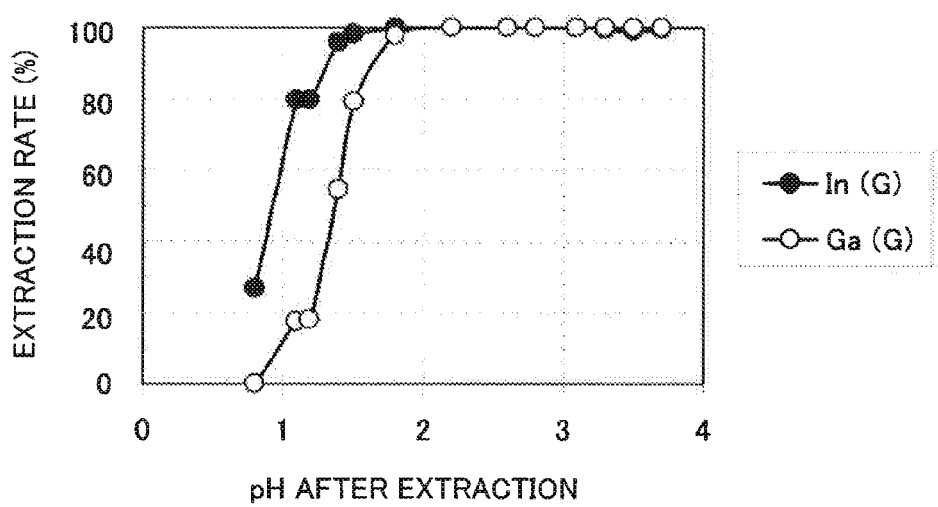
FIG. 3 shows the results when indium was extracted from an acidic solution containing indium and gallium using an extraction agent comprising a glycine amide derivative.

After shaking, the aqueous phase was separated and the concentration of indium and the concentration of gallium were measured using an inductively coupled plasma-atomic emission spectrophotometer (ICP-AES). In addition, the organic phase was subjected to back extraction using 2 mol/l nitric acid. The concentration of indium and the concentration of gallium in the back extraction phase were measured using ICP-AES. Using these measurement results, the extraction rates of indium and gallium were defined by the amount of material in the organic phase/(the amount of material in the organic phase+the amount of material in the aqueous phase) and obtained. The results are shown in FIG. 3. In FIG. 3, the abscissa is the pH of a sulfuric acidic solution and the ordinate is the extraction rate of indium or gallium (unit: %). In the graph, a closed circle indicates the extraction rate of indium and an open circle indicates the extraction rate of gallium.

Example 2

Figure 4:
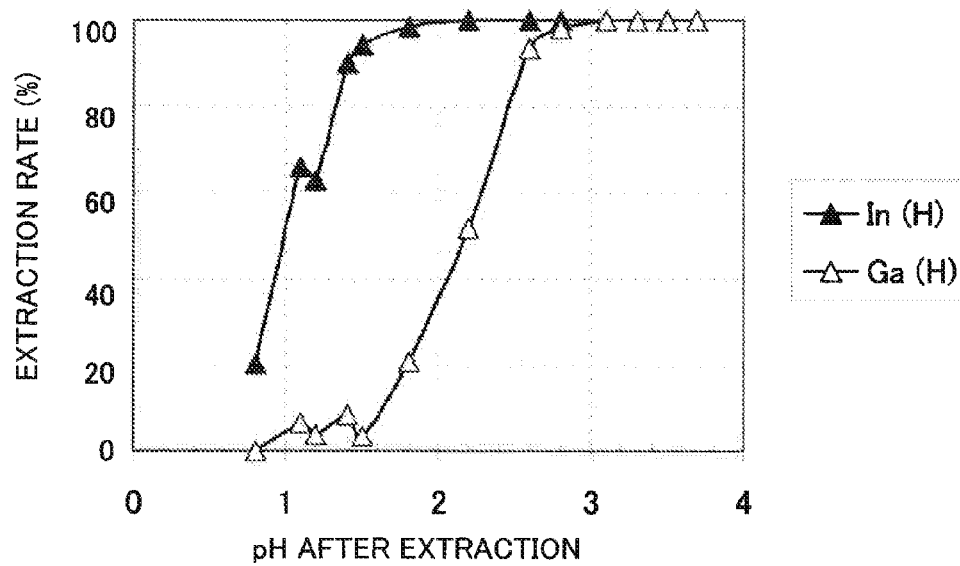
FIG. 4 shows the results when indium was extracted from an acidic solution containing indium and gallium using an extraction agent comprising a histidine amide derivative.

Indium was extracted from a sulfuric acidic solution containing indium and gallium in the same method as in Example 1 except that the extraction agent involved in Synthetic Example 2 was used as the extraction agent in place of the extraction agent involved in Synthetic Example 1. The results are shown in FIG. 4. In FIG. 4, the abscissa is the pH of sulfuric acidic solution and the ordinate is the extraction rate of indium or gallium (unit: %). In the graph, a closed triangle indicates the extraction rate of iridium and an open triangle indicates the extraction rate of gallium.

Example 3

Figure 5:
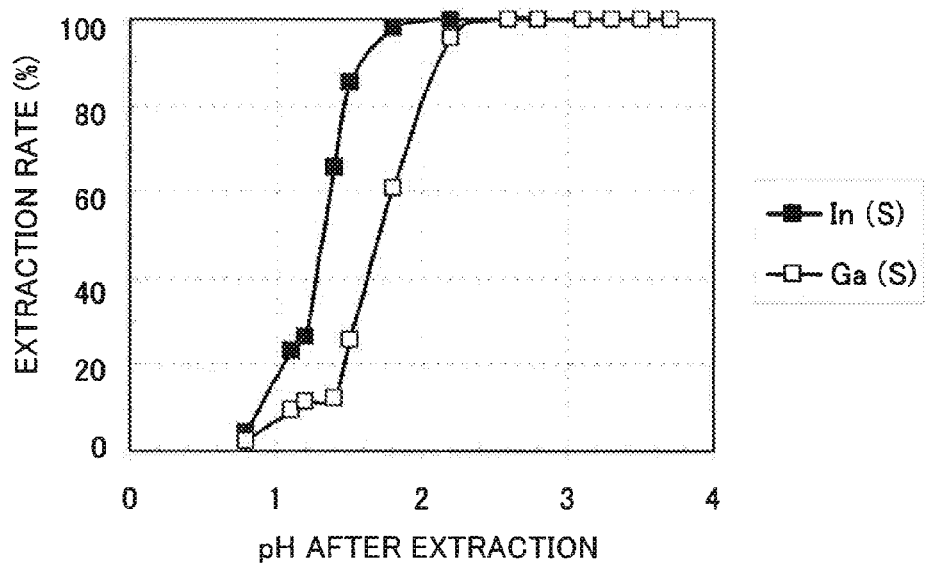
FIG. 5 shows the results when indium was extracted from an acidic solution containing indium and gallium using an extraction agent comprising a normal-methylglycine derivative.

Indium was extracted from a sulfuric acidic solution containing indium and gallium in the same method as in Example 1 except that the extraction agent involved in Synthetic Example 3 was used as the extraction agent in place of the extraction agent involved in Synthetic Example 1. The results are shown in FIG. 5. In FIG. 5, the abscissa is the pH of a sulfuric acidic solution and the ordinate is the extraction rate of indium or gallium (unit: %). In the graph, a closed square indicates the extraction rate of indium and an open square indicates the extraction rate of gallium.

Figure 6:
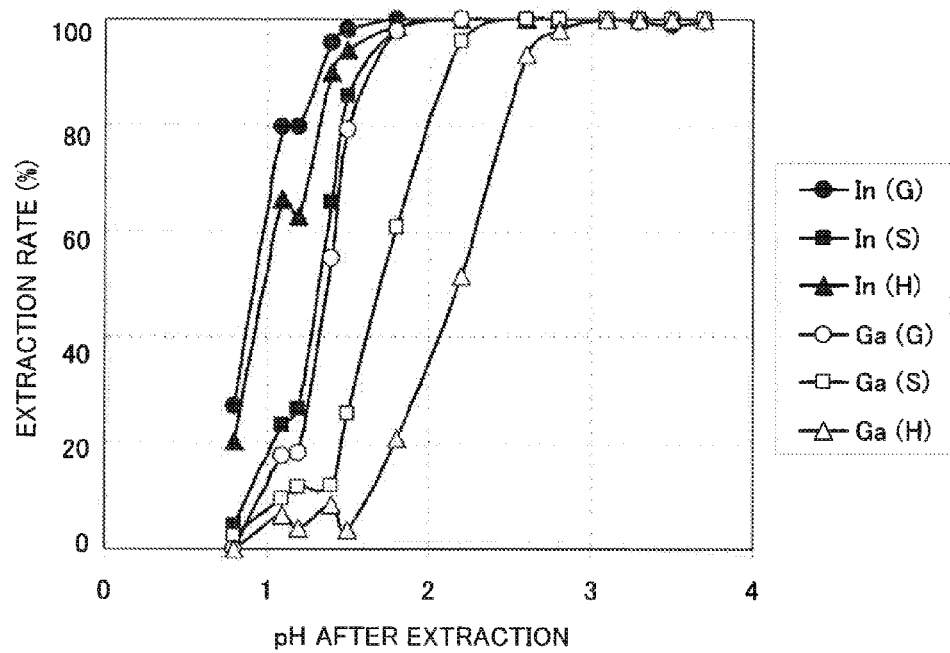
FIG. 6 is a diagram summarizing the results shown in FIG. 3 to FIG. 5 in a graph.

It was verified that indium could be efficiently extracted from a sulfuric acidic solution containing indium and gallium using the extraction agents in Synthetic Examples 1 to 3 (FIG. 3 to FIG. 5). In addition, the differences depending on types of extraction agent are considered, and it is thought that an extraction agent comprising a histidine amide derivative is industrially more preferred than an extraction agent comprising a glycine amide derivative or a normal-methylglycine derivative with respect to which both the extraction of indium at a high concentration and the inhibition of gallium extraction can be achieved in a wide pH range as shown in FIG. 6.

Furthermore, extraction agents using amino acids having a lysine amide derivative and an aspartic acid amide derivative as a main component can be considered. The extraction behaviors of these agents are the same as when using the extraction agents involved in Synthetic Examples 1 to 3 in view of complex stability constants thereof. Therefore, it is inferred that indium can be efficiently isolated.

Figure 7:
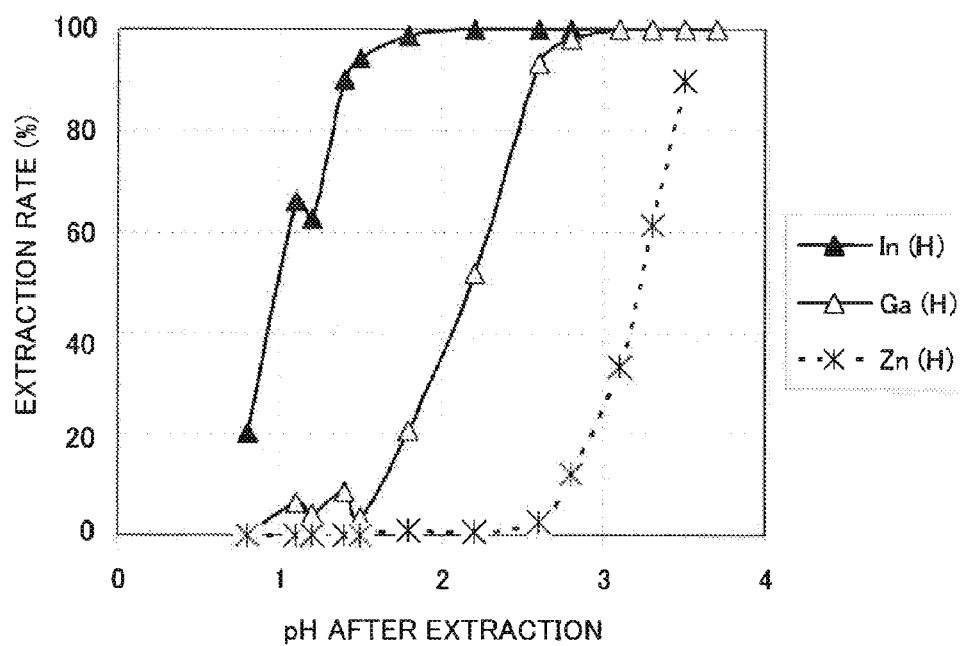
FIG. 7 is a diagram showing the relation between pH and the extraction rates of indium, gallium and zinc when an extraction agent comprising a histidine amide derivative is used.

As described above, among the extraction agents involved in the present invention, an extraction agent comprising a histidine amide derivative can isolate indium and gallium in a particularly wide pH range. Using this property, zinc, indium and gallium can be isolated from each other using an extraction agent comprising a histidine amide derivative when zinc is also contained in an acidic solution containing indium and gallium. FIG. 7 is a diagram showing the relation between pH and the extraction rates of metal elements (indium, gallium and zinc). As can be seen from the description of FIG. 7, indium and gallium are extracted while the pH of an acidic solution containing indium, gallium and zinc is successively raised, and the three components can be isolated by leaving zinc in the residual liquid of extraction. For example, when an acidic solution to be extracted is adjusted to between pH 0.8 or more and 1.5 or less and brought into contact with an extraction agent, indium is selectively extracted. Next, when the pH of the acidic solution after indium is extracted is adjusted to between 2.6 or more and 3.0 or less and brought into contact with an extraction agent using a histidine amide derivative, which is different from the above, gallium is extracted this time, and indium and gallium can each be isolated by separating them from zinc which has not been extracted. In addition, from the same idea, the pH of the above acidic solution containing indium, gallium and zinc is raised to, for example, a value of about 2.6 to 3.0 to extract indium and gallium, and only gallium is then selectively back-extracted by adding a new acid solution adjusted to pH 0.8 to 1.5 to the extraction agent, and thus indium is isolated, and the metal elements can be isolated from each other.

The invention claimed is:

1. A method for isolating a valuable metal, wherein an acidic solution having an acidic pH and containing indium and gallium is subjected to solvent extraction by an extraction agent comprising an amide derivative represented by the following general formula (I) to isolate indium and gallium from the acidic solution:

$$\begin{array}{c} R^1 \\ \diagdown \\ R^2 \end{array} N \begin{array}{c} \\ \\ \| \\ O \end{array} \begin{array}{c} R^4 \\ | \\ N \\ | \\ R^3 \end{array} \begin{array}{c} \\ \\ \| \\ O \end{array} OH \qquad (I)$$

wherein $R^1$ and $R^2$ each represent the same or different alkyl group,
the alkyl group is optionally a straight chain or a branched chain,
$R^3$ represents a hydrogen atom or an alkyl group, and
$R^4$ represents a hydrogen atom or any group other than an amino group which is bonded to an α chain as an amino acid.

2. The method for isolating a valuable metal according to claim 1, wherein the amide derivative is any one or more of a glycine amide derivative, a histidine amide derivative, a lysine amide derivative, an aspartic acid amide derivative and a normal-methylglycine derivative.

3. The method for isolating a valuable metal according to claim 2, wherein the amide derivative is the glycine amide derivative, and
the pH of the acidic solution is adjusted to a range of between 0.7 to 1.9.

4. The method for isolating a valuable metal according to claim 3, wherein the acidic solution containing indium and gallium is a solution obtained by mixing sulfuric acid with a member containing indium and gallium and not containing cadmium and leaching indium and gallium from the member.

5. The method for isolating a valuable metal according to claim 3, wherein, an acidic solution with a pH of 0.6 or less is mixed with the extraction agent which has extracted the indium, and, thereafter, the extraction agent and the acidic solution are separated to obtain the acidic solution containing the indium.

6. The method for isolating a valuable metal according to claim 2,
wherein the amide derivative is the histidine amide derivative, and
the pH of the acidic solution is adjusted to a range of between 0.7 to 3.0.

7. The method for isolating a valuable metal according to claim 6, wherein, an acidic solution with a pH of 0.6 or less is mixed with the extraction agent which has extracted the indium, and, thereafter, the extraction agent and the acidic solution are separated to obtain the acidic solution containing the indium.

8. The method for isolating a valuable metal according to claim 6, wherein the acidic solution containing indium and gallium is a solution obtained by mixing sulfuric acid with a member containing indium and gallium and not containing cadmium and leaching indium and gallium from the member.

9. The method for isolating a valuable metal according to claim 2,
wherein the amide derivative is the normal-methylglycine derivative, and
the pH of the acidic solution is adjusted to a range of between 0.7 to 2.3.

10. The method for isolating a valuable metal according to claim 9, wherein, an acidic solution with a pH of 0.6 or less is mixed with the extraction agent which has extracted the indium, and, thereafter, the extraction agent and the acidic solution are separated to obtain the acidic solution containing the indium.

11. The method for isolating a valuable metal according to claim 9, wherein the acidic solution containing indium and gallium is a solution obtained by mixing sulfuric acid with a member containing indium and gallium and not containing cadmium and leaching indium and gallium from the member.

12. The method for isolating a valuable metal according to claim 2, wherein, an acidic solution with a pH of 0.6 or less is mixed with the extraction agent which has extracted the indium, and, thereafter, the extraction agent and the acidic solution are separated to obtain the acidic solution containing the indium.

13. The method for isolating a valuable metal according to claim 1, wherein an acidic solution with a pH of 0.6 or less is mixed with the extraction agent which has extracted the indium and, thereafter, the extraction agent and the acidic solution are separated to obtain the acidic solution containing the indium.

14. The method for isolating a valuable metal according to claim 13, further comprising mixing an acidic solution mixed with the extraction agent which has extracted the indium, and the extraction agent and the acidic solution are then separated to remove the gallium from the extraction agent.

15. The method for isolating a valuable metal according to claim 14,
wherein the amide derivative is a glycine amide derivative, and
the acidic solution has a pH of between 1.1 and 1.4.

16. The method for isolating a valuable metal according to claim 15, wherein the acidic solution containing indium and gallium is a solution obtained by mixing sulfuric acid with a member containing indium and gallium and not containing cadmium and leaching indium and gallium from the member.

17. The method for isolating a valuable metal according to claim 14,
wherein the amide derivative is a histidine amide derivative, and
the acidic solution has a pH of between 1.5 and 1.8.

18. The method for isolating a valuable metal according to claim 14,
wherein the amide derivative is a normal-methylglycine derivative, and
the acidic solution has a pH of between 1.4 and 1.8.

19. The method for isolating a valuable metal according to claim 14, wherein the acidic solution containing indium and gallium is a solution obtained by mixing sulfuric acid with a member containing indium and gallium and not containing cadmium and leaching indium and gallium from the member.

20. The method for isolating a valuable metal according to claim 13, wherein the acidic solution containing indium and gallium is a solution obtained by mixing sulfuric acid with a member containing indium and gallium and not containing cadmium and leaching indium and gallium from the member.

* * * * *